United States Patent [19]

Colliec et al.

[11] Patent Number: 5,321,133

[45] Date of Patent: Jun. 14, 1994

[54] SULPHATED POLYSACCHARIDES, ANTICOAGULANT AGENT AND ANTICOMPLEMENTARY AGENT OBTAINED FROM BROWN ALGAE FUCUSES AND METHOD OF OBTAINING SAME

[75] Inventors: Sylvia Colliec; Jacqueline Bretaudiere, both of Paris; Patrick Durand, Reze; Anne-Marie Fischer, Paris; Jacqueline Jozefonvicz, Lamorlaye; Bernard Kloareg, Saint-Pol-De-Leon; Catherine Vidal, Paris, all of France

[73] Assignee: Institut Francais de Recherche pour l'Exploitation de la Mer-IFREMER, Issy-Les-Moulineaux, France

[21] Appl. No.: 778,220

[22] PCT Filed: Jun. 13, 1990

[86] PCT No.: PCT/FR90/00420

§ 371 Date: Jan. 16, 1992

§ 102(e) Date: Jan. 16, 1992

[87] PCT Pub. No.: WO90/15823

PCT Pub. Date: Dec. 27, 1990

[30] Foreign Application Priority Data

Jun. 14, 1989 [FR] France .................. 89 07857

[51] Int. Cl.$^5$ .................. C08B 31/00; A61K 31/715
[52] U.S. Cl. .................. 536/118; 514/834; 536/127
[58] Field of Search .................. 424/195.1; 536/118, 536/127; 514/54, 822, 834

[56] References Cited

U.S. PATENT DOCUMENTS 4,581,233 4/1986 Hervé et al. .................. 424/195.1

FOREIGN PATENT DOCUMENTS 890207 2/1962 United Kingdom .

OTHER PUBLICATIONS

Patent Abstracts of Japan, vol. 10, No. 219 (C-363)(2275), Jul. 31, 1986, JP 61-57520 dated Mar. 24, 1986 to Kibun Food Chemiphar K.K.

B. Larsen, et al., "Sulphated Polysaccharides in Brown Algae", *Acta Chemica Scandinavica*, vol. 24, No. 9, 1970, pp. 3339-3352.

T. Nishino, et al., "Isolation, Purification, and Characterization of Fucose Containing Sulfated Polysaccharides from the Brown Seaweed *Ecklonia kurome* And Their Blood-Anticoagulant Activities", *Carbohydrate Research*, vol. 186, No. 1, Feb. 15, 1989, pp. 119-129.

F. C. Church, et al., "Antithrombin Activity of Fucoidan", *The Journal of Biological Chemistry*, vol. 264, No. 6, Feb. 25, 1989, pp. 3618-3623.

*Primary Examiner*—Ronald W. Griffin
*Attorney, Agent, or Firm*—Bell, Seltzer, Park & Gibson

[57] ABSTRACT

The invention relates to sulphated polysaccharides obtained from fucuses extracted from pheophyceae. The molecular weight of these polysaccharides is greater than 5 and less than 40 Kda; their sulphur content is greater than that of the original fucus and they contain less than 0.15% of contaminant proteins. Applications as anticoagulant and anticomplementary agents.

25 Claims, 2 Drawing Sheets

SULPHATED POLYSACCHARIDES, ANTICOAGULANT AGENT AND ANTICOMPLEMENTARY AGENT OBTAINED FROM BROWN ALGAE FUCUSES AND METHOD OF OBTAINING SAME

The present invention relates to novel sulphated polysaccharides, obtained by controlled lysis of the fucans extracted from Phaeophyceae (brown algae), to the process for obtaining them, as well as to a novel anticoagulant and antithrombotic agent and a novel anticomplement agent.

The anticoagulant effect is defined as the inhibition of the formulation of active thrombin in the plasma, while the antithrombotic effect is defined as the inhibition of the formation of the thrombus and/or of its growth.

The anticoagulant drug most used at present is heparin, which is a sulphated polysaccharide consisting of 1→4-linked glucosamine and glucuronic acid units, in which the sulphate groups are present on the amine function of the glucosamine, and/or on alcohol functions of the glucoseamine and uronic acid. Heparin acts on the coagulation by boosting the anticoagulant action of two plasma inhibitors. The first, which is antithrombin III (AT III), acts both on thrombin (also known as factor IIa) and on activated factor X (or factor Xa); the second, called heparin cofactor two (HC II), acts on factor IIa, and not on factor Xa.

Moreover, as regards the prevention of thrombosis, heparins of low molecular weight obtained by depolymerization are being increasingly used- their action on the overall coagulation is weak; for example, they have no effect in vitro on the cephalin kaolin time (CKT), which examines in a global fashion the plasma coagulation by the endogenous pathway, that is to say all the plasma factors with the exception of factor VII and the platelet factors; in contrast, they permit in vivo the prevention of experimental thromboses. It has been shown that they boosted the inhibitory activity of AT III with respect to factor Xa, and that their activity with regard to factor IIa was low. However, it seems more and more probable that their action in the prevention of thromboses is exerted essentially by their low residual anti-IIa activity.

Heparin is also known for its anticomplement properties. The complement system is a set of plasma or membrane proteins which play an important role in the immune defence mechanism. It participates in the defence of the organism (destruction of infectious agents, clearance of immune complexes) and in pathological processes of an inflammatory type. In the blood it is additionally responsible for haemolysis or lysis of the red cells.

The complement proteins are in an inactivated forum in the serum. They are activated in a specific order in two sequences, the alternative pathway and the classical pathway. The activation of the alternative pathway is based on a non-specific mechanism of recognition of the target surface (bacteria, virus, parasite, tumour cell). The activation of the classical pathway is based on the specific recognition of the target by an antibody. In the alternative pathway, the initial phase is triggered by the fixation of a product of cleavage of C3 (C3b) and the release of C3a, anaphylatoxin responsible for inflammatory reactions. The C3b thus binds by covalent bonding to hydroxyl and amino groups on the surface. Once bound, it can bind factor B and, after activation of the latter by factor D, it forms the alternative C3 convertase. In the classical pathway, the initial phase is triggered by activation of C1, which is effected principally at the level of an antigen-antibody complex. After activation of C1, components C4 and C2 are in turn activated and form on the surface an enzymatic complex, classical C3 convertase. The activation of C4 is analogous to that of C3 with release of C4b and C4a. C4b fixes in a covalent manner to the same type of chemical groups as C3b.

Heparin acts as an inhibitor of the activation of the complement by its interaction with C3 convertase. It has been shown that this anticomplement activity of heparin is totally independent of its antithrombic (sic) activity and that it is associated with the presence on the amine function of a sulphate or acetyl group, in contrast to the anticoagulant activity which is not observed if the substituent of the amine function is not a sulphate group. It also appears that the presence of a sulphate group on one of the alcohol functions of the uronic acid plays an important role in the anticomplement activity [KAZATCHINE et al.; J. Clin. Invest.; 67, (1981)).

Other polysaccharides are also known for their anticoagulant and/or antithrombotic properties; these are, for example, dermatan sulphates, whose anticoagulant activity is weak compared to that of heparin, but whose antithrombotic activity is equivalent. They act by inhibiting thrombin, by boosting the inhibitory effect of cofactor HC II; in contrast, they do not act by way of cofactor AT III and have no effect on factor Xa.

Pentosan polysulphate, widely used in the prevention of thromboses, also acts by catalysing the inhibition of thrombin by HC II.

On the other hand, these polysaccharides do not exhibit an anticomplement activity comparable to that of heparin; KAZATCHINE et al. have shown, in the publication cited hereinabove, that dermatan sulphate, in which the amine function of the galactosamine is acetylated, but in which the alcohol functions of the uronic acid are not sulphated, is in this respect fourteen times less active than heparin.

The fucans are sulphated polysaccharides of high mean molecular weight (100 to 800 kDa), extracted from the thalli of brown algae. They are polymers of α-1,2-L-fucose 4-sulphate which may also contain D-xylose, D-galactose and uronic acids. The uronic acids of the fucans are not sulphated, in contrast to those of heparin. Further-more, the fucans differ both from heparin and from dermatan sulphate in that they do not contain amino sugars.

In studies carried out on crude fucans, it has been possible to separate from one and the same crude extract various subpopulations of fucans, differing from one another on the one hand in terms of their mean molecular weight and on the other hand in terms of their physicochemical properties.

These studies, using non-aggressive fractionation procedures (fractionated precipitation, gel filtration, etc. . . .), which do not degrade the polysaccharide skeleton of the fucan molecules, have in fact revealed the existence of natural subpopulations of fucans.

The anticoagulant properties of the crude fucans were demonstrated in 1957 by SPRINGER et al. and have since been confirmed by numerous authors [BERKUDI and SPRINGER, The Journal of Biological Chemistry, 237.1, (1962); MORI et al., Marine Algae in Pharmaceutical Science, 2, 1982]

A study carried out by the inventors, on the mechanism of action of crude fucan on coagulation, has shown that crude fucan prolongs the cephalin kaolin time (CRT) and especially the thrombin time (TT) (which examines the conversion of fibrinogen to a fibrin clot under the influence of thrombin, last phase of coagulation). This study also shows that the crude fucan acts almost exclusively on thrombin (factor IIa), and this chiefly by boosting the effect of the HC II inhibitor (at the same concentration as heparin), and that of antithrombin III (at concentrations 30 times greater than those of heparin). on the other hand, in contrast to heparin, fucan has no anti-Xa activity.

Similar observations have been made by other authors [CHURCH et al. The Journal of Biological Chemistry; 264.6 (1989)) who have also studied the properties of crude fucan. These authors have raised (sic) that crude fucan weakly catalyses the inhibition of thrombin by AT III and strongly catalyses the inhibition of thrombin by HC II.

The fucans could therefore constitute a new category of novel anticoagulant drugs by virtue of their mechanism of action, which differs from that of the known anticoagulants. They in fact boost the inhibitory activity Of HC II and also that of AT III with respect to thrombin, in contrast to dermatan sulphate which boosts exclusively the inhibitory activity of HC II only. On the other hand, the fucans, like dermatan sulphate and in contrast to heparin, have no effect on the inhibition of factor Xa; they are exclusive Inhibitors of thrombin, The invents-re have also noted that the fucans, although (in contrast to heparin) containing no amino sugars or O-sulphated uronic acids, Surprisingly have the property of inhibiting the activation of the complement.

The complement activation inhibitors can play a role in the prevention of transplant rejection phenomena; their use has also been proposed in the treatment of those undergoing renal dialysis and those recovering from myocardial infarction. Benefit may also be derived from the anticomplement activity for inhibiting the activation of the complement in extracorporeal circulation devices.

Although their anticoagulant properties have been known for many years, crude fucans have not been used in therapy, on the one hand on account of their relatively high residual protein content, which risks provoking immunogenic phenomena, and on the other hand on account of their high molecular weight which results in a poor solubility, which considerably limits their use at high concentrations.

Now, the studies carried out to date on the anticoagulant action of fucans, in particular those concerning the anticoagulant activity of the various fucan subpopulations obtained by fractionation of the crude fucan, suggested that the anticoagulant activity was associated precisely with the large size of the fucan molecules. Some teams reached the conclusion that the anticoagulant activity was related to a high molecular weight [USUI et al. Agr., Biol. Chem., 44-8, (1980)].

Other studies are in agreement in establishing the existence of a lower limit of 20 kDa, below which no significant anticoagulant activity has been observed. British Patent 890,207 describes, for example, the obtaining of 7 different fractions, whose molecular weights range between 5 and 50,000, by fractionated precipitation of the crude fucan using ethanol. According to this patent, among these fractions only those whose molecular weight is greater than 20,000 exhibit a noteworthy anticoagulant activity.

NISHINO et al. [Carbohydrate Research, 186 (1989); 119-129] have studied the anticoagulant properties of the fractions obtained from non-degraded fucans and have also established this limit of 20 kDa; moreover, the purified fractions described in their publication have a mechanism of action different from that described for crude fucans, because although, like the latter, they seem to be more active on thrombin than on factor Xa, their action manifests itself essentially in the overall mechanism of the coagulation, which is reflected in a prolongation of the cephalin kaolin time (CKT); in is contrast, they have only a slight effect on the thrombin time and therefore appear leas active in the last phase of coagulation.

It thus appears that the polysaccharide subpopulations obtained hitherto by non-degrading fractionation of the crude fucan have an action on coagulation which is variable from one subpopulation to another and which may, it seems, be different from that observed in the case of the crude fucan; on the other hand, i t emerges from the work carried out to date that the fractions of molecular weight lower than 20 KDa, which would be particularly advantageous for their solubility, have virtually no effect on the coagulation.

The inventors have put forward the hypothesis that, by fragmenting the long polysaccharide chains of the crude fucan, it would be possible to obtain fractions of low molecular weight; however, the cutting of the saccharide skeleton of the fucan molecules necessitates the use of lysis processes which is necessary to be able to control so as to avoid an excessive degradation of the fucan, resulting in the loss of its properties.

The experiments already carried out in this direction had not permitted the development of a process for degradation of fucans affording fractions of intermediate molecular weight; indeed, the processes used resulted either in insufficient degradation, affording fractions of molecular weight greater than 40 kDa, or almost total degradation, affording fragments devoid of anticoagulant activity [V.COLLIEC et al., IVémes Journées d'hémostase et de thrombose, paria, March 1988], [FISCHER et al., International Congress on thrombosis (Athens), May 1988), [COLLIEC et al., Polymers in Medicine, Warsaw, October 1988).

Consequently, the aim of the present invention is to provide for polysaccharide fractions of relatively low molecular weight obtained by controlled lysis from the fucans of brown algae; it also aims to provide for anticoagulant and antithrombic agents which are particularly advantageous in that their activity is exerted by inhibition of factor IIa and in that they do not possess any anti-Xa activity, and in that they do not exhibit the side effects due to the high molecular weight and to the high residual protein content of the crude fucans, and which are furthermore obtained from brown algae which are raw materials readily available in great quantity. It also aims to provide for a novel anticomplement agent obtained from the fucans of brown algae.

The present invention relates to sulphated polysaccharides obtained from the fucans of Phaeophyceae, characterized in that their molecular weight, determined by gel filtration compared to a polysaccharide standard, is greater than 5 and less than 40 kDa, in that their sulphur content is greater than that of the original fucan, in that they contain less than 0.15% of contaminant proteins and in that they are more soluble than the original fucans, and in that they have anticoagulant and antithrombotic properties.

Sulphated polysaccharides according to the invention can be obtained by controlled lysis of a crude fucan extracted from Phaeophyceae.

According to a preferred embodiment of the sulphated polysaccharides according to the invention, their mean molecular weight is less than or equal to 20 kDa.

According to another preferred embodiment of the sulphated polysaccharides according to the invention, their mean molecular weight is between 20 and 35 kDa.

According to a likewise preferred embodiment of the sulphated polysaccharides according to the invention, their sulphur content is 2% to 20% greater than that of the original fucans.

According to a particularly advantageous arrangement of this embodiment, the sulphated polysaccharides are obtained by controlled acid hydrolysis from fucans extracted from *Fucus vesiculosus*, their sulphur content is about 15% to 20% greater than that of the original fucans and their protein content is less than 0.05%.

According to another particularly advantageous arrangement of this embodiment, the sulphated polysaccharides are obtained by controlled acid hydrolysis from fucans extracted from *Ascophyllum nodosum*, their sulphur content is about 24 to 5% greater than that of the original fucans and their protein content is leas than 0.05%.

According to another particularly advantageous arrangement of this embodiment, the sulphated polysaccharides are obtained by controlled acid hydrolysis from fucans extracted from *Pelvetia canaliculata*, their sulphur content is about 15% to 20% greater than that of the original fucans, and their protein content is less than 0.05%.

According to yet another particularly advantageous arrangement of this embodiment, the sulphated polysaccharides are obtained by controlled acid hydrolysis from fucans extracted from *Undaria pinnatifida*, their sulphur content is about 10% to 15% greater than that of the original fucans, and their protein content is less than 0.05%.

The inventors demonstrated, in vitro and in vivo, that the sulphated polysaccharides according to the invention had both anticoagulant and antithrombic (sic) properties. In contrast to the polysaccharide sub-populations of low molecular weight described by NISHINO et al., the polysaccharides according to the invention act essentially in the last phase of coagulation.

The present invention also relates to an anticoagulant and antithrombotic agent, active both in vitro and in vivo, activator of cofactors HCII and AT III, characterized in that it comprises at least one sulphated polysaccharide as defined hereinabove.

The present invention furthermore relates to a process for obtaining the sulphated polysaccharides as defined hereinabove,, characterized in that a controlled lysis of a crude fucan originating from Phaeophyceae is carried out, in that the lysate obtained is fractionated by gel filtration, and in that fractions of molecular weight greater than 5 and less than 40 kDa are recovered.

According to a preferred mode of implementation of the process according to the present invention, the controlled lysis of the fucan is carried out by acid hydrolysis.

According to a particularly advantageous arrangement of this mode of implementation, the acid hydrolysis is effected by the action of 0.5 to 1N $H_2SO_4$, at a temperature of between 40° and 50° C. for 1 to 4 hours.

According to another preferred mode of implementation of the process according to the present invention, the controlled lysis of the fucan is effected by radiolysis, by subjecting the fucan to an irradiation, particularly by gamma rays.

According to yet another preferred mode of implementation of the process according to the present invention, the controlled lysis of the fucan is carried out by enzymatic hydrolysis. This mode of implementation involves the use of at least one enzyme capable of fragmenting the hydrocarbon skeleton of the fucan, for example an enzyme of the $\alpha$-1-2-fucosidase type; mixtures of enzymes, which are made up for example of the gastric juices of sea molluscs or obtained from the latter, or else of enzymes contained in bacteria which degrade the algae, can also be used.

According to yet another preferred mode of implementation of the process according to the present invention, the controlled lysis of the fucan is carried out by physical processes, in particular by sonication.

According to an advantageous mode of implementation of the process according to the invention, the fractions whose molecular weight is less than or equal to 20 kDa are recovered.

The molecular weight of the sulphated polysaccharides according to the present invention permits their solubilization, even at high concentration, in the plasma and in injectable solutions. Moreover, compared to the crude fucans, they contain a low percentage of contaminant proteins. It is therefore possible to use these products in man as drugs. This is particularly advantageous in certain applications of the antithrombotic properties of the sulphated polysaccharides according to the invention, in particular in the prevention of venous thromboses by subcutaneous injection of an antithrombotic agent; this application requires the use of relatively concentrated solutions, which was impossible with the non-fractionated fucans; it is also conceivable to use the sulphated polysaccharides according to the invention orally and transdermally.

The fractions having a molecular weight of between 5 and 100 kDa, obtained from the fucans, moreover have an anticomplement activity equal to or greater than that of the non-fractionated fucans.

The present invention thus also relates to an agent inhibiting the activation of the complement, characterized in that it comprises fucans extracted from Phaeophyceae and/or their fractions.

According to a preferred embodiment of the agent inhibiting the activation of the complement according to the present invention, it comprises a fraction having a molecular weight greater than 50 kDa, obtained from a fucan extracted from Phaeophyceae.

According to a preferred embodiment of the agent inhibiting the activation of the complement according to the present invention, it comprises a fraction having a mean molecular weight of between 5 and 50 kDa, obtained from a fucan extracted from Phaeophyceae.

According to another preferred embodiment of the agent inhibiting the activation of the complement according to the present invention, it comprises sulphated polysaccharides as defined hereinabove.

The present invention will be better understood from the remaining description which follows and which refers to examples of obtaining sulphated polysaccharides according to the present invention from fucans extracted from various brown algae, and to the demonstration of the activities of these polysaccharides.

However, it should be clearly understood that these examples are given merely by way of illustration of the subject of the invention, and they in no way constitute a limitation thereof.

I—OBTAINING SULPHATED POLYSACCHARIDE FRACTIONS ACCORDING TO THE INVENTION

Example 1: Fractionation of the Fucans and Purification of the Fractions Obtained A) Extraction of fucans from brown algae.

The fucans are extracted from the parietal material of the thalli of brown algae by means of a conventional organic extraction procedure. This procedure is derived from the procedure as per BLACK at al., [J. Sci. Food Agric. (1952)].

The extraction protocol can be outlined as follows: the thalli are ground in absolute ethanol containing 5% by weight of formal. The ground mixture obtained is subjected to a first extraction, using 95% ethanol containing 5% by weight of formal, then to a second extraction using a 2/1 (V/V) acetone/toluene mixture. After drying in an oven, the material obtained is subjected to one or more acid extractions using 0.01M HCl containing 2% by weight of $CaCl_2$.

After neutralization using sodium hydroxide, the acid extract is treated with N-cetylpyridinium chloride which forms a complex with the most highly sulphated fucans and thus makes it possible to enrich the preparation with the latter. The precipitate obtained is subsequently redissolved in a 3M $CaCl_2$ solution and is then freeze-dried.

B) Fractionation of the extracted fucans.

1st step: degradation of the crude extract.

a) by acid hydrolysis

The acid extract is dissolved at a rate of 10 mg/ml in a 1N $H_2SO_4$ solution and the temperature is fixed at 45° C. The degradation followed by viscosimetry (Ubbelohde-type viscometer with a flow tube diameter of 0.5 mm) is stopped by addition of sodium hydroxide solution (M NaOH) before total hydrolysis of the fucan. During the degradation, the reduced specific viscosity ($\eta$ spec./c) is calculated every 30 minutes. The solution of degraded acid extract is concentrated, subjected to ultrafiltration using a membrane having a cut-off threshold of 1,000 daltons, and finally freeze-dried.

b) by radiolysis

The radiochemical hydrolysis is carried out under irradiation from a 60,000 Ci cobalt-60 source. The crude fucans are irradiated at room temperature for 92 hours at a dosage rate of 2081 rads/minute or an irradiation dose of 11.5 Mrads for all the samples.

C) Enzymatic degradation

The enzymatic degradation of the crude extract of *Pelvetia canaliculata* using crude extracts of gastric juice from a haliotis (*Haliotis tuberculata*) and an aplysia (*Aplysia californica*) is carried out as follows: the crude fucan is dissolved at a concentration of 10 mg/mL in citrate phosphate buffer, pH 5.8 (citric acid=0.1M $C_5H_8O_7$ and disodium hydrogen phosphate=0.2M $Na_2HPO_4.2H_2O$). The fucan solution is heated to 37° C. and 200 μl of gastric extract are added every hour to ensure a constant concentration of active enzyme. The degradation is followed by viscosimetry, the reduced specific viscosity, ($\eta$sp)/C, is calculated at the time of the various samplings. The reaction is stopped by addition of a 0.2M solution of disodium carbonate ($Na_2CO_3$).

2nd step: preparative fractionation of the degraded crude extract a) on the laboratory scale 500 mg of lyophilizate taken up in 5 ml of 0.2M NaCl are deposited on a column (height 35 to 45 cm × 4.8 cm) of fractionation gel (SEPHACRYL S-200 or S-300). The linear flow rate is 3.33 cm/hour. A double detection is carried out at the outlet of the column using a differential refractometer and an UV detector at 280 nm. The column was calibrated using polysaccharide standards. The signals are recorded on a dual channel recorder. After studying the chromatograms, the various fractions obtained at the outlet of the column (5 ml) are combined in 3 or 4 fractions. Each fraction is concentrated, subjected to ultrafiltration on a membrane having a cut-off threshold of 10,000 daltons for the first fraction and a membrane having a cut-off threshold of 1,000 daltons for the other fractions, and is freeze-dried.

b) on semi-pilot scale 30 g of lyophilisate taken up in 125 ml of 0.2M NaCl are deposited on a SEPHACRYL S-200 column (height 60 cm × diameter 11.3 cm), the linear flow rate is 15 cm/hour. A double detection is carried out at the outlet of the column using a differential refractometer and an UV detector at 280 nm. The signals are recorded on a dual channel recorder. After studying the chromatograms, the various fractions obtained at the outlet of the column (30 ml) are combined in 3 or 4 fractions. Each fraction is concentrated, subjected to ultrafiltration on a membrane having a cut-off threshold of 10,000 daltons for the first fraction and a membrane having a cut-off threshold of 1,000 daltons for the other fractions, and is freeze-dried.

Figure 1:
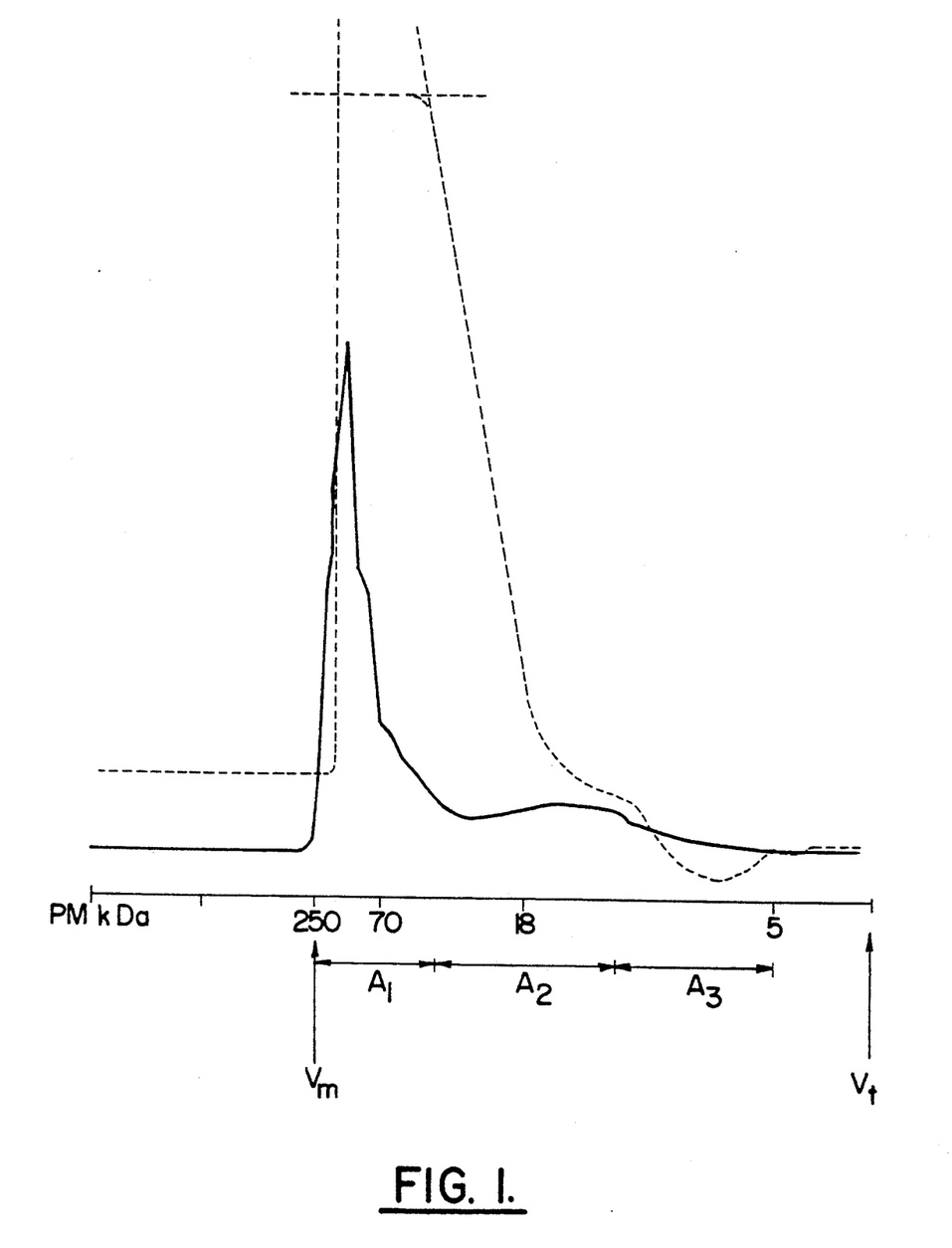
FIG. 1 shows the preparative fractionation on SEPHACRYL S-200 gel (fractionation range $250 \times 10^3$ to $5 \times 10^3$ daltons) of the fucan acid extract degraded using 1N $H_2SO_4$ at 45° C.

FIG. 1 shows the preparative fractionation on SEPHACRYL S-b 200 gel (fractionation range $250 \times 10^3$ to $5 \times 10^3$ daltons) of the fucan acid extract degraded using 1N $H_2SO_4$ at 45° C.: $A_1$=1st fraction (MW>20 kDa); $A_2$=2nd fraction (20 kDa>MW>10 kDa); $A_3$ 3rd fraction (MW>10 kDa); Vd=dead volume and Vt=total volume. The curve in a broken line (----) represents the quantity of eluted material measured by differential refractometry. The curve in a full line (—) represents the quantity of proteins measured by UV absorption at 280 nm.

Example 2: Physicochemical Characterization of the Fractions Obtained

Figure 2A:
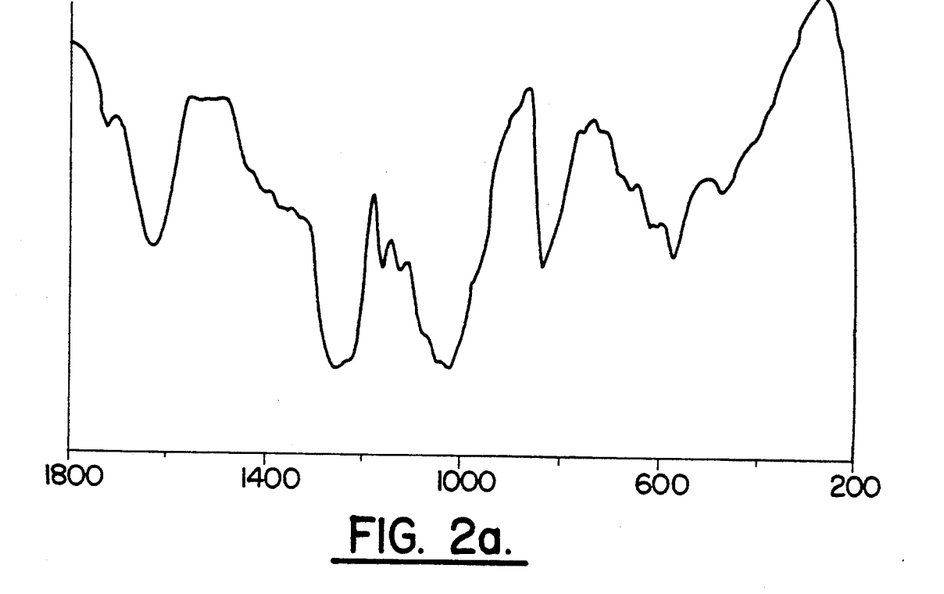
FIGS. 2a) and 2b) show the infrared spectra of the crude fucan (2a) extracted from the walls of *Fucus vesiculosus* and of an $A_e$ fraction (2b) of mean molecular weight $13 \times 10^3$ obtained by controlled acid hydrolysis of this acid extract.
Figure 2B:
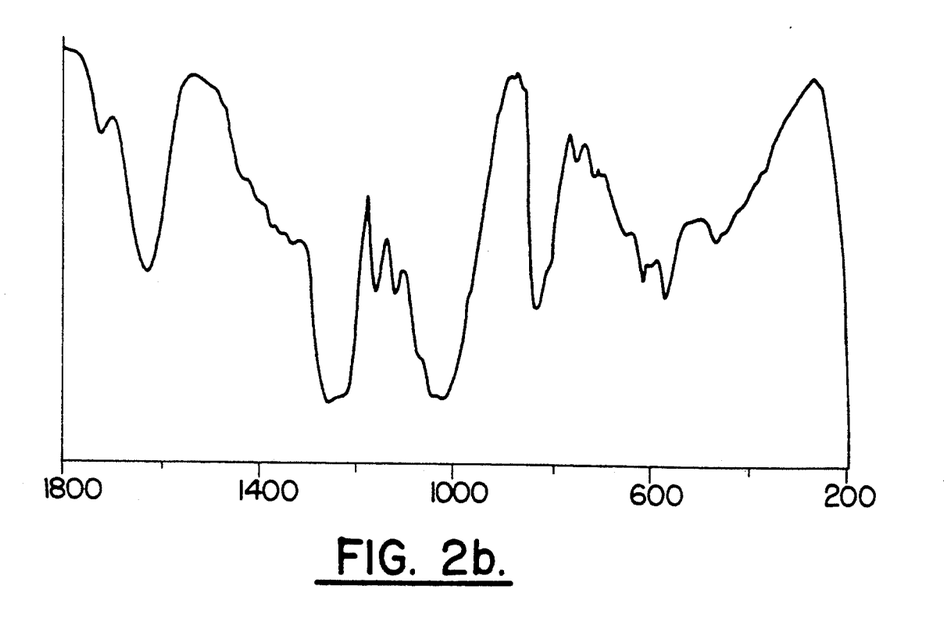

Infrared spectrum:

FIGS. 2A and 2B show the infrared spectra of the crude fucan (2a) extracted from the walls of *Fucus vesiculosus* and of an $A_2$ fraction (2b) of mean molecular weight $13 \times 10^3$ obtained by controlled acid hydrolysis of this acid extract. The peak at 1240 $cm^{-1}$ is characteristic of the sulphuryl groups. The peak at 850 $cm^{-1}$ shows that the majority of the sulphate groups are in the $C_4$ position on the L-fucose; however, some of these sulphate groups are in the $C_6$ position, as shown by the shoulder at 820 cm$^{-1}$. The majority of the carboxylic functions are in nondissociated form, as shown by the peak at 1720 cm$^{-1}$, compared to the weak shoulder at 1420 cm$^{-1}$ which represents the carboxylic functions in dissociated form.

Determination of the molecular weight:

The determination of the molecular weight in g/mole of the fucan fractions is carried out by analytical high-performance liquid chromatography (HPLC) on a Si-Diol 500 column (fractionation range 5,000 to $10^6$ daltons) by injection of 50 μl of standard polysaccharides (pullulane from POLYMER LABORATORIES LTV.) or of the fucan fraction studied, at 2 mg/ml in 0.2N NaCl, the flow rate being 1 ml/mm and the detection carried out by refractometry. The chromatograms are stored and then analyzed using a microcomputer having a GPC program (steric exclusion chromatography on permeable gel), and the results are recorded on a printer.

S and N content:

The S and N content of the fucan fractions is given in % (by weight of pure product) by elemental analysis.

Protein content:

The protein content is estimated in % (by weight of pure product) using the Bradford colorimetric test ("Bio-Rad" test) taking bovine albumin as a reference.

Table I allows a comparison to be made between the physicochemical properties of the crude fucan, that is to say of the non-fractionated acid extract (AE)f and of the sulphated polysaccharides according to the present invention, represented by the $A_2$ fraction obtained by acid hydrolysis from the crude fucans extracted from 4 brown algae: (*Ascophyllum nodosum* (An), *Fucus vesiculosus* (Fv), *Pelvetia canaliculata* (Pc), *Undaria pinnatifida* (UP).

TABLE I

|  | Mean molecular weight | S % | Protein % | Yield % |
|---|---|---|---|---|
| AE (An) | 7 × 10$^5$ | 8.9 | 0.36 | — |
| A2 (An) | 18 × 10$^3$ | 9.1 | <0.01 | 57 |
| AE (Fv) | 8 × 10$^5$ | 7.8 | 0.85 | — |
| A2 (Fv) | 13 × 10$^3$ | 9.2 | <0.01 | 57 |
| AE (Pc) | 75 × 10$^4$ | 9.4 | 0.19 | — |
| A2 (Pc) | 18 × 10$^3$ | 11 | <0.01 | 40 |
| AE (Up) | 48 × 10$^4$ | 7.2 | 0.26 | — |
| A2 (Up) | 23 × 10$^3$ | 8.0 | <0.01 | 36 |

Table II allows a comparison to be made between the physicochemical properties of then on-fractionated acid extract (AE) and of the sulphated polysaccharides according to the present invention, represented by the $A_2$ fraction obtained by radiolysis from the fucans of 3 brown algae: (*Ascophyllum nodosum* (An), *Fucus vesiculosus* (Fv), *Pelvetia calaliculata* (Pc).

TABLE II

|  | Mean molecular weight | S % | Protein % | Yield % |
|---|---|---|---|---|
| AE (An) | 7 × 10$^5$ | 8.9 | 0.36 | — |
| A2 (An) | 17 × 10$^3$ | 7.8 | 0.11 | 46 |
| AE (Fv) | 8 × 10$^5$ | 7.8 | 0.85 | — |
| A2 (Fv) | 17 × 10$^3$ | 8.6 | <0.01 | 56 |
| AE (Pc) | 75 × 10$^4$ | 9.4 | 0.19 | — |
| A2 (Pc) | 15 × 10$^3$ | 9.7 | 0.10 | 58 |
| AE (Up) | 48 × 10$^4$ | 7.2 | 0.26 | — |
| A2 (Up) | 13 × 10$^4$ | 8.0 | 0.11 | 36 |

II—COMPARISON OF THE BIOLOGICAL ACTIVITY OF THE CRUDE FUCANS AND OF THE FRACTIONS OBTAINED BY CONTROLLED LYSIS OF THE LATTER

Example 3: Anticoagulant Activity In Vitro

The anticoagulant activity of the non-degraded fucan and of fractions of degraded fucan of molecular weight between 10 and 20 kDa is evaluated using the cephalin kaolin time (CKT). The activity is given in international units per mg of product (IU/mg), by the following relationship: (slope of the straight line of the fucan fraction/slope of the straight line of the standard heparin) x activity in IU/mg of the standard heparin (Heparin H108 from laboratories CHOAY).

The slope is calculated from the straight line obtained by plotting the logarithm of the coagulation time in seconds, as a function of the anticoagulant concentration (concentration of heparin 0.5 to 1 μg/ml of plasma, and of fucan 10 to 50 μg/ml).

Table III allows a comparison to be made between the anti-coagulant activities of the acid extract (AE), (or crude fucan), and of the $A_2$ fraction (obtained by acid hydrolysis) of the brown algae: (An), *Ascophyllum nodosum* (An), *Fucus vesiculosus* (Fv), *Pelvetia canaliculata* (Pc) and *Undaria pinnatifida* (Up).

TABLE III

|  | Anticoagulant activity* (IU/mg) |
|---|---|
| AE (An) | 4.5 |
| A2 (An) | 6.6 |
| AE (Fv) | 5.0 |
| A2 (Fv) | 5.8 |
| AE (Pc) | 4.0 |
| A2 (Pc) | 2.0 |
| AE (Up) | — |
| A2 (Up) | 1.3 |

*Anticoagulant activity determined by taking as reference a standard heparin H108 at 173 IU/mg.

Table IV permits a more precise analysis of the anticoagulant action of the sulphated polysaccharides according to the invention, by allowing a comparison between the respective effects on the Quick time (QT), the cephalin kaolin time (CKT), the thrombin time (TT), and the reptilase time (RT) of the $A_2$ fraction (Pc) and of heparin.

TABLE IV

|  | Coagulation time (seconds) | | | |
|---|---|---|---|---|
|  | QT | CKT | TT | RT |
| F2 (PC) (sic) (μg/ml) | | | | |
| 0 | 13 | 56 | 25 | 22 |
| 10 | 14 | 70 | 40 | 22 |
| 25 | 15 | 100 | 130 | 22 |
| 30 | 15 | 120 | >180 | 21 |
| 50 | 15 | 155 | >180 | 22 |
| 100 | 18 | 220 | >180 | 22 |
| Heparin (μg/ml) | | | | |
| 0.25 | 14 | 85 | 90 | 22 |
| 0.5 | 14 | 120 | >120 | 22 |

TABLE II-continued

|  | Mean molecular weight | S % | Protein % | Yield % |
|---|---|---|---|---|
| A2 (Up) | 13 × 10$^4$ | 8.0 | 0.11 | 36 |

TABLE IV-continued

|  | Coagulation time (seconds) | | | |
| --- | --- | --- | --- | --- |
|  | QT | CKT | TT | RT |
| 0.75 | 14 | 150 | >120 | 22 |
| 1 | 14 | >200 | >120 | 22 |
| 5 | 17 | >200 | >120 | 22 |
| 10 | 23 | >200 | >120 | 22 |

This shows that the sulphated polysaccharides according to the invention are essentially active on the thrombin time.

Example 4: Anticoagulant Activity In Vivo; Influence of the Sulphated Polysaccharides According to the Invention on the Coagulation Parameters The anticoagulant activity in vivo; influence of the sulphated polysaccharides according to the invention on the coagulation parameters The anticoagulant activity of the polysaccharide fractions according to the present invention is evaluated in the rabbit. A fraction having a mean molecular weight of 15,000 Da prepared according to the acid hydrolysis process described in Example 1 is injected into rabbits weighing 3 kg. The rabbits are bled at regular intervals and the coagulation parameters are evaluated on the blood withdrawn, by measurement of the thrombin time (TT) and that of the cephalin kaolin time (CKT).

Table V shows the change in the coagulation parameters as a function of time, after injection of 0.5 ml of a solution of sulphated polysaccharides according to the present invention (fraction A2 (sic) of *Ascophyllum nododum*, obtained by acid hydrolysis), at 100 mg/ml, 40 mg/ml, 30 mg/ml, and by way of comparison after injection of heparin at 2 mg/ml.

TABLE V

|  | Sampling time | TT (sec.) | CKT (sec.) |
| --- | --- | --- | --- |
| $A_2$ (An) | 0 | 35 | 23.3 |
| 100 mg/ml | 10 min | >240 | 115 |
|  | 30 min | >240 | 88.4 |
|  | 4 h 30 | 31 | 32.4 |
| $A_2$ (An) | 0 | 48 | 30 |
| 40 mg/ml | 10 min | >240 | 73.4 |
|  | 30 min | >240 | 58.8 |
|  | 4 h 30 | 23.4 | 25 |
| $A_2$ (An) | 0 | 33 | 25 |
| 30 mg/ml | 10 min | >300 | 59.2 |
|  | 30 min | 123.6 | 47 |
|  | 4 h 30 | 20.3 | 24 |
| Heparin | 0 | 28.4 | 23 |
|  | 10 min | >240 | 52 |
|  | 30 min | >240 | 60 |
|  | 4 h 30 | — | — |

Example 5: Antithrombotic Activity In Vivo; Experimental Thrombosis

I. Method

The experimental thrombosis model used is that of WESSLER and HAUPTMANN [STANFORD WESSLER, STANLEY M. REIMER and MINDEL C. SHEPS—J. Appl. Physiol. (1959) 14 p 943-946] in the rabbit, which model uses factor Xa J. HAUPTMANN, B. KAISER, F. MARKWARDT and G. NOUAK—Thromb. Haemostaris (six) Stuttgart 43 (1980) p. 118-123, as the agent triggering thrombosis.

The tests are carried out with a polysaccharide fraction having a mean molecular weight of 20,000±2,000 obtained by acid hydrolysis of the crude fucan, as described in Example 1. The product is injected intravenously at doses of 0.150; 0.625; 1.25; 2.5 and 5 mg/kg 10 min before induction of thrombosis. Each dose is tested on 5 rabbits. A determination of the antithrombotic ED50 (Effective Dose 50, corresponding to the dose which reduces by 50% the weight of the thrombus formed) was carried out by logarithmic regression and reveals a mean value of 0.40 mg/kg (between 0.23 and 0.66 mg/kg).

The blood sampling is carried out 10 minutes after the intravenous injection just after the creation of the various clump. The mean results obtained for each dose am summarized in Table VI.

TABLE VI

| Dose injected (mg/kg) | $CKT^a$ (sec.) | $TT^b$ (sec.) | $QT^c$ (sec.) |
| --- | --- | --- | --- |
| 0 | 30.6 | 20.4 | 8.5 |
| 0.150 | 31.8 | 22.2 | 8.5 |
| 0.625 | 35 | 24.9 | 8.7 |
| 1.25 | 40.2 | 38.5 | 8.6 |
| 2.5 | 50.9 | 45.2 | 8.5 |
| 5 | 67.6 | 71.2 | 8.4 |
| Controls | 28.8 | 21.4 | 8.3 |

[a] Cephalin kaolin time
[b] Thrombin time
[c] Quick time

These results confirm those observed in vitro and reported in Example 3 and in Table IV.

The results observed in the control rabbits which were subjected to the experimental thrombosis protocol, but which received only the solvent of the $A_2$ fraction, are also indicated in this table. The mean weights of the wet thrombin taken from the contralateral vein are indicated in Table VII for doses of 0.15; 0.625; 1.25 and 5 mg/kg.

TABLE VII

| Dose (mg/kg) | 5 | 1.25 | 0.625 | 0.15 | Controls |
| --- | --- | --- | --- | --- | --- |
| Weight of thrombus (mg) | 0.0 | 0.0 | 23.5 | 40 | 76.9 |

Example 6: Determination of the Overall Anticomplement Activity of the Fucans and of Their Fractions The anticomplement activity is determined by assay of the HC50 (haemolytic complement 50), in the presence or in the absence of fucans. The HC50 assay permits assessment of the overall functional activity of the classical pathway of the complement system of human serum. This test consists in determining the smallest amount of freshly recovered human serum capable of bringing about the lysis of 50% of a given number of red cells from sheep, which cells are sensitized in an optimum manner by rabbit antibodies against sheep red cells (Se=sensitized erythrocytes).

The proteins of the classical pathway of the complement system recognize these red cells as a foreign element and are activated by successive cleavages to react to these red calls, which brings about the lysis of the latter. It is possible to determine the inhibition properties of a polymer such as heparin or fucan by assaying the HC50 in the presence of the polymer. The inhibition capacity is given by the concentration in mg of polymer per ml of human serum diluted ¼ capable of inhibiting 50% of the lysis of the cells, by establishing a dose/response curve for the lysis of the cells as a function of the polymer concentration. The weaker the latter, the greater the anticomplement activity of the polymer. To measure the anticomplement activity of the fucans, the acid extract (crude fucan) as well as fractions of different molecular weights obtained by acid hydrolysis of the said crude fucan were used. The experimental conditions are as follows:

50 µl of pure NHS (normal human serum) are mixed with 50 µl of fucan at different concentrations (0.2 to 0.5 mg/ml); after incubation for 30 minutes at 37° C., 4,900 µl of VBS++ buffer are added. Solution A is obtained.

Moreover, 0.3 to 0.8 ml of VBS++ buffer are mixed with 0 to 0.5 ml of solution A, to obtain a total volume of 0.8 ml; 0.2 ml of sensitized erythrocytes are added to the mixture; after incubation for 45 minutes at 37° C., the mixture is centrifuged for 10 min at 1,300 g and at 4° C., and the reading of the OD is carried out at 414 mm.

| Composition of the VBS++ buffer: | |
|---|---|
| Nacl (sic) | 42.5 g |
| Veronal (sodium diethylbarbital) | 1.875 g |
| Diethylbarbituric acid | 2.85 g |
| Distilled H₂O, q.s. | 1,000 ml |

The pH is adjusted to 7.4; 20 ml of this solution are mixed with 80 ml of distilled water: 0.5 ml of 0.03M CaCl₂ and 0.5 ml of 0.10M MgCl₂ are added.

The results obtained are shown in Table VIII (2nd column). The fucan fractions are 3 to 100 times more active than heparin H108 analyzed under the same conditions. This activity is independent of the anticoagulant activity.

TABLE VIII

| Fractions | ID$_{50}$ (HC50) (mg/ml) | ID$_{50}$ C3a (mg/ml) | ID$_{50}$ C4a (mg/ml) |
|---|---|---|---|
| AE An | 0.036–0.16 | nd | 0.14 |
| A$_1$ An | 0.26 | 0.070 | nd |
| A$_2$ An | 1–1.37 | 0.10 | 0.11 |
| A$_3$ An | 0.20 | 0.175 | 0.024 |
| A$_1$ Pc | 0.036 | nd | nd |
| A$_2$ Pc | 0.60 | nd | nd |
| A$_2$ Fv | 1.95 | nd | nd |
| A$_2$ Up | 1.26 | nd | nd |
| Heparin | 4 | 0.15 | 0.05 |

It is thus shown that the crude fucan as well as the fractions having a mean molecular weight of between 5 and 100 kDa totally inhibit the activation of the complement and have an anticomplement activity greater than that of heparin. Indeed, while in the case of heparin 4 mg/ml of polymer are needed to inhibit 50% of the lysis of the calls, only 0.035 to 1.95 mg/ml (depending on the molecular weight) of crude or fractionated fucans are needed to obtain the same effect. It has thus been observed that fractions having a mean molecular weight of 18,000 kDa, prepared an described in Example 1, inhibit 50% of the lysis of the calls at a concentration of 1.3 mg/ml and that fractions having a mean molecular weight of between 5 and 10 kDa inhibit 50% of the lysis of the cells at a concentration of 0.20 mg/ml.

Example 7: Measurement of C3a and C4a by Radioimmunassay

The concentration of the proteins C3a and C4a liberated in fluid phase during the activation is measured in the supernatant by radioimmunoassay determination (sic).

The assay is carried out in the following manner using the C3a-desarg 125I radioimmunoassay kit (marketed by Amersham).

50 µl of pure NHS activated by Sephadox are mixed with 50 µl of VBS++ buffer and 100 µl of fucan at variable concentrations (0.1 to 5 mg/mi); the mixture is incubated for 30 minutes at 37° C. and then centrifuged for 5 min at 1,700 g. 160 µl of supernatant are removed, to which 10 µl of EDTA ($8.66 \times 10^{-2}$M) are added (which blocks the activation of the complement), then 170 µl of precipitating agent (provided with the assay kit); after incubation for 5 minutes at room temperature, the mixture is centrifuged for 2 minutes at 10,000 g and the supernatant is diluted (¼ to 1/512) before proceeding to the RIA.

The activity of the sample (ID50) is expressed as the amount of fucan necessary to inhibit 50% of the amount of C3a normally generated in 1 ml of NHS diluted ¼. this inhibitory dose in expressed in mg of fucan/ml of NHS diluted ¼. The results are shown in Table VIII (column 3).

A solution of 0.21 mg/ml of A₂(An) in NHS diluted ¼ permits a reduction of the activation of C3 below the spontaneous activation of NHS.

In addition, 0.5 mg of the same fraction suffices to inhibit totally the activation of the C3 contained in 1 ml of NHS diluted ¼ and subjected to an activator (Sephadex, which brings about, at the concentration of 15 mg/ml, a total activation of the complement) in a amount greater than that necessary for a total activity of the complement.

The results relating to C4a are also shown in Table VIII (column 4).

An emerges from the preceding text, the invention is in no way limited to those of its modes of implementation, embodiments and modes of application which have just been described in greater detail; on the contrary, it includes all the variants thereof which can occur to the person skilled in the art, without departing from the framework or from the scope of the present invention.

We claim:

1. Sulphated polysaccharides, obtained from fucans extracted from Phaeophyceae, characterized in that they are obtained by controlled lysis of a crude fucan extacted from Phaeophycaea, in that their molecular weight, determined by gel filtration compared to a polysaccharide standard, is greater than 5 and less than 40 kDa, in that their sulphur content is greater than that of the original fucan, in that they contain less than 0.15% of contaminant proteins and in that they are more soluble than the original fucans, and in that they have anticoagulant and antithrombotic properties.

2. Sulphated polysaccharides according to claim 1, characterized in that their mean molecular weight is less than or equal to 20 kDa.

3. Sulphated polysaccharides according to claim 1, characterized in that their mean molecular weight is between 20 and 35 kDa.

4. Sulphated polysaccharides according to claim 1, characterized in that their sulphur content is 2% to 20% greater than that of the original fucans.

5. Sulphated polysaccharides according to claim 4, characterized in that they are obtained by controlled acid hydrolysis from fucans extracted from *Fucus vesiculosus*, in that their sulphur content is about 15% to 20% greater than that of the original fucans and in that their protein content is less than 0.05%.

6. Sulphated polysaccharides according to claim 4, characterized in that they are obtained by controlled acid hydrolysis from fucans extracted from *Ascophyllum nodosum*, in that their sulphur content is about 2% to 5% greater than that of the original fucans and in that their protein content is less than 0.05%.

7. Sulphated polysaccharides according to claim 4, characterized in that they are obtained by controlled acid hydrolysis from fucan extracted from *Pelvetia canaliculata*, in that their sulphur content is about 15% to 20% greater than that of the original fucans and in that their protein content is less than 0.05%.

8. Sulphated polysaccharides according to claim 4, characterized in that they are obtained by controlled acid hydrolysis from fucans extracted from *Undaria pennatifida*, in that their sulphur content is about 10% to 15% greater than that of the original fucans and in that their protein content is less than 0.05%.

9. Anticoagulant and antithrombotic agent, active both in vitro and in vivo, activator of cofactors HCII and AT III, characterized in that it consists essentially of at least one sulphated polysaccharide, according to claim 1.

10. Agent inhibiting the activation of the complement, characterized in that is consists essentially of fucans extracted from Phaeophyceae and/or their fractions.

11. Agent inhibiting the activation of the complement, according to claim 10, characterized in that it comprises a fraction having a molecular weight greater than 50 kDa, obtained from a fucan extracted from Phaeophyceae.

12. Agent inhibiting the activation of the complement according to claim 10, characterized in that it comprises a fraction having a mean molecular weight of between 5 and 50 kDa, obtained from a fucan extracted from Phaeophyceae.

13. Agent inhibiting the activation of the complement, characterized in that it consists essentially of sulphated polysaccharides, according to claim 1.

14. A process for obtaining sulphated polysaccharides from fucan originating from Phaeophyceae which comprises; controlling lysis of a crude fucan, recovering the lysate, fractionating the lysate by gel filtration, and recovering the fractions having a molecular weight greater than 5 kDa and less than 40 kDa.

15. The process according to claim 14 wherein the controlled lysis of the fucan is carried out by acid hydrolysis.

16. The process according to claim 15 where said acid hydrolysis is effected by the action of 0.5 to 1N $H_2SO_4$ at a temperature of between 40° C. and 50° C. for 1 to 4 hours.

17. The process according to claim 14 wherein said controlled lysis of the fucan is effected by radiolysis, by subjecting the fucan to irradiation.

18. The process according to claim 14 wherein said controlled lysis of the fucan is carried out by enzymatic hydrolysis.

19. The process according to claim 14 wherein said controlled lysis of the fucan is carried out by physical processes.

20. The process according to claim 14 wherein said fractions whose molecular weight is between 20 kDa and 35 kDa are recovered.

21. The process according to claim 14 wherein said fractions whose molecular weight is between 20 kDa and 35 kDa are recovered.

22. The process according to claim 14 wherein said crude fucan is obtained from *Fucus vesiculosus*.

23. The process according to claim 14 wherein said crude fucan is obtained from *Ascophyllum nodosum*.

24. The process according to claim 14 wherein said crude fucan is obtained from *Pelvetia canaliculata*.

25. The process according to claim 14 wherein said crude fucan is obtained from *Undaria pinnatifida*.

* * * * *

UNITED STATES PATENT AND TRADEMARK OFFICE
CERTIFICATE OF CORRECTION

PATENT NO. : 5,321,133

DATED : June 14, 1994

INVENTOR(S) : Sylvia Colliec et al.

It is certified that error appears in the above-identified patent and that said Letters Patent is hereby corrected as shown below:

Column 2, line 22, "(1981))" should be -- (1981)] --.

Column 2, line 49, "Further-more" should be -- Furthermore --.

Column 2, lines 65-66, "BERKUDI" should be -- BERNARDI --.

Column 3, line 12, "on" should be -- On --.

Column 3, line 16, "(1989))" should be -- (1989)] --.

Column 3, line 25, "Of" should be -- of --.

Column 3, line 30, "Inhibitors" should be -- inhibitors --.

Column 3, line 31, the comma "," (first occurrence) should be a period -- . --.

Column 3, line 31, "invents-re" should be -- inventors --.

Column 3, line 33, "Surprisingly" should be -- surprisingly --.

Column 4, line 3, the "(1989);" should be -- (1989), --.

Column 4, line 13, delete "is".

UNITED STATES PATENT AND TRADEMARK OFFICE
CERTIFICATE OF CORRECTION

PATENT NO. : 5,321,133

DATED : June 14, 1994

INVENTOR(S) : Sylvia Colliec et al.

It is certified that error appears in the above-identified patent and that said Letters Patent is hereby corrected as shown below:

Column 4, line 22, "i t" should be -- it --.

Column 4, line 43, "paria" should be -- Paris --.

Column 4, line 45, "1988)" should be -- 1988] --.

Column 4, line 46, "1988)" should be -- 1988] --.

Column 4, line 51, "antithrombic" should be -- antithrombotic --.

Column 5, line 27, "24" should be -- 2% --.

Column 5, line 28, "leas" should be -- less --.

Column 5, line 58, after "hereinabove" delete the comma -- , -- (second occurrence).

Column 7, line 5, "$A_c$" should be -- $A_2$ --.

Column 7, line 28, "at" should be -- et --.

Column 7, lines 32 and 34, "formal" should be -- formol --.

Column 7, line 66, "C)" should -- c) --.

UNITED STATES PATENT AND TRADEMARK OFFICE
CERTIFICATE OF CORRECTION

PATENT NO. : 5,321,133
DATED : June 14, 1994
INVENTOR(S) : Sylvia Colliec et al.

It is certified that error appears in the above-identified patent and that said Letters Patent is hereby corrected as shown below:

Column 8, line 17, "lyophilizate" should be -- lyophilisate --.

Column 8, line 49, "S-b 200" should be -- S-200 --.

Column 8, line 52, after "$A_3$" insert -- = --.

Column 9, line 3, "$C_6$" should be -- $C_5$ --.

Column 9, line 16, "LTV" should be -- LTD --.

Column 9, line 17, "0.2N" should be -- 0.2M --.

Column 9, line 32, "(AE)f" should be -- (AE), --.

Column 9, line 38, "(UP)" should be -- ($u_p$) --.

Column 9, line 53, "then on-fractionated" should be -- the non-fractionated --.

Column 10, line 32, delete "(An),".

Column 11, lines 16-18, "The anticoagulant activity in vivo; influence of the sulphated polysaccharides according to the invention on the coagulation parameters" should be deleted.

Column 11, line 63, "(six)" should be -- (sic) --.

UNITED STATES PATENT AND TRADEMARK OFFICE
CERTIFICATE OF CORRECTION

PATENT NO. : 5,321,133
DATED : June 14, 1994
INVENTOR(S) : Sylvia Colliec et al.

It is certified that error appears in the above-identified patent and that said Letters Patent is hereby corrected as shown below:

Column 12, line 11, "am" should be -- are --.

Column 13, line 57, "an" should be -- as --.

Column 13, line 64, "Radioimmunassay" should be -- Radioimmunoassay ---.

Column 14, line 4, "Sephadox" should be -- Sephadex --.

Column 14, line 6, "mg/mi" should be -- mg/ml --.

Column 14, line 34, "An" should be -- As --.

Column 14, line 46, "Phaeophycaea" should be -- Phaeophyceae --.

Column 15, line 17, "pennatifida" should be -- pinnatifida --.

Column 15, line 27, "is" should be -- it --.

UNITED STATES PATENT AND TRADEMARK OFFICE
CERTIFICATE OF CORRECTION

PATENT NO.  : 5,321,133
DATED       : June 14, 1994
INVENTOR(S) : Sylvia Colliec et al.

It is certified that error appears in the above-identified patent and that said Letters Patent is hereby corrected as shown below:

Column 16, line 13, "where" should be -- wherein --.

Column 16, lines 26-28, should read as follows:

-- 20. The process according to claim 14 wherein said fractions whose molecular weight greater than 5kDa and less than or equal to 20kDa are recovered --.

Signed and Sealed this

Twenty-second Day of November, 1994

Attest:

BRUCE LEHMAN

Attesting Officer

Commissioner of Patents and Trademarks